United States Patent [19]

Schreiber

[11] Patent Number: 4,889,486

[45] Date of Patent: Dec. 26, 1989

[54] DEVICE FOR MOUNTING JAW CASTS IN AN ARTICULATOR

[76] Inventor: Hans Schreiber, Mierendorfstrasse 2, 6940 Weinheim, Fed. Rep. of Germany

[21] Appl. No.: 147,192

[22] Filed: Jan. 22, 1988

[30] Foreign Application Priority Data

Jan. 24, 1987 [DE] Fed. Rep. of Germany ... 8701173[U]
Aug. 19, 1987 [DE] Fed. Rep. of Germany ... 8711262[U]

[51] Int. Cl.$^4$ ............................................. A11C 11/60
[52] U.S. Cl. ..................................................... 433/60
[58] Field of Search ..................................... 433/60, 61

[56] References Cited

U.S. PATENT DOCUMENTS

664,830 1/1901 Bryan .................................... 433/60
4,715,815 12/1987 Rossner ................................. 433/60

Primary Examiner—Robert Peshock
Attorney, Agent, or Firm—Staas & Halsey

[57] ABSTRACT

A device for mounting for mounting jaw casts in an articulator, has a spatially adjustable cast plate, an articulator base plate, and wedges that can be moved longitudinally and transversely. The wedges can be rotated axially, and fixation elements can be moved like a sled in the inclination of the wedges. The fixation elements can be locked in a predetermined position by screwing in the inclination of the wedges, with the cast plate being pressed against the wedges and fixed.

28 Claims, 13 Drawing Sheets

DEVICE FOR MOUNTING JAW CASTS IN AN ARTICULATOR

BACKGROUND OF THE INVENTION

The invention relates to a device for mounting jaw casts in an articulator in the most widely used articulator systems.

To prepare dental plates or crowns and bridges, the casts made are fixed or mounted in socalled articulators for further treatment.

The conventional medium of attachment is plaster, which permits a spatial allocation of the casts. However, a great disadvantage here is the expansion of the plaster, that is to say, during crystallization (i.e., during the curing), it is impossible to control the change in volume of the plaster, thus resulting in an undesirable tolerance of the work result. Among other drawbacks is the long setting time of the plaster.

The mounting with plaster of casts in an articulator results, during the setting phase, in an expansion of the plaster because of the crystallization process. The degree of this plaster expansion is dependent upon the height of the plaster base. Laboratories operating with a high degree of precision minimize this effect by mounting the casts in several layers of plaster, which, naturally multiplies the already time-consuming setting time of the plaster, and this is another drawback.

Also, the resultant soiling of the articulators, particularly because it is often necessary to knock out the casts after the work has been completed, leads to damage of the precision instruments.

An incorrect occlusal position can be rectified only by removing one of the plaster bases and mounting the corresponding jaw cast by means of plaster in an articulator after another registration. This time-consuming procedure calls in most cases for another session for the patient, and there is still no guarantee at all that, after another corrective session, the patient has obtained the correct occlusal position during the last registration.

Other disadvantages are: the plaster support plates of the articulators can be reused only a few times, the mixing of the plaster alone results in a loss of time and makes subsequent clean-up operations necessary.

SUMMARY OF THE INVENTION

Therefore, the object of the invention is to provide a device which dispenses with one or with both plaster bases, inasmuch as the cast plate, and thereby the cast fixed thereon, can be mounted in an articulator by mechanical means alone and, because of the nature of its construction, exerts no additional mounting pressure on the geometric position of the casts, so that the device can be used with almost any articulator known from the prior art.

The instant invention has the following individual objects:

1. preventing the plaster from expanding;
2. enabling the dentist to obtain a correct occlusal position with ease on the dental chair.
3. obtaining a fairly high degree of precision of the denture work;
4. reducing the cost even in cases where the casts are made by the laboratory, since the possibility is provided to set up an extra session for checking and, if necessary, correcting the occlusal position, that is not detrimental to the patient;
5. providing the possibility of compatibility with the most widely used articulator systems;
6. mounting, in an articulator, both conventional casts and more recent cast systems;
7. protection of expensive articulators;
8. prevention of loss of time loss due to the mixing of plaster and subsequent clean-up work;
9. providing a device that can be reused many times.

These objects can be achieved, according to the invention, inasmuch as the device for mounting jaw casts in an articulator consists of a spatially adjustable cast plate, an articulator base plate, and wedges that can be moved longitudinally and transversely and rotated axially and has fixation elements that can slidably move in the inclination of the wedges and can be locked in a certain position by screwing in the inclination of the wedges, with the cast plate being pressed on the wedges and fixed.

A particularly preferred embodiment is characterized by the fact that the cast plate carries a positive or negative relief, which permits the direct plastering of jaw casts, is further suited to receive cast systems, whereby, by means of a magnet or other fixation aids, a removal and safe setting back of the plaster casts on to the cast plate is possible.

Another particularly preferred embodiment is characterized by the fact that the base plate is provided on either side with a guide slot.

Another particularly preferred embodiment is characterized by the fact that the wedge has an inclination face provided with a slotted hole that is open at the top and has side bars on which the fixation element can be slidably moved, and that there is provided in the bottom region a slotted hole which serves for the mounting to the base plate.

Still another particularly preferred embodiment is characterized by the fact that the wedges, preferably through spring bias of a screw running in the slot guide of the base plate and guided spin-safe through a screw milling, are located with allowance for adjustment and can be fixed through the slotted hole of the wedge bottom on the baseplate by means of a wing nut or a knurled nut.

Another particularly preferred embodiment is characterized by the fact that the fixation element is formed as a sliding plate with a retainer clamp which is bent away in the lower region.

Another particularly preferred embodiment is characterized by the fact that the fixation element is formed as a sliding plate with a retainer clamp which is bent away in the upper region.

Another particularly preferred embodiment is characterized by the fact that the fixation element is formed as a sliding plate with a retainer clamp which are bent away in the upper and lower regions.

Another particularly preferred embodiment is characterized by the fact that the fixation element has a threaded bore.

Another particularly preferred embodiment is characterized by the fact that the fixation element has a threaded pin mounted on the bearing face.

Another particularly preferred embodiment is characterized by the fact that the cast plate has a trapezoidal shape and has a milling provided on either side to locate the retainer clamp.

Another particularly preferred embodiment is characterized by the fact that the cast plate has a rib for fixing the cast plate by means of the retainer clamp.

Another particularly preferred embodiment is characterized by the fact that the base plate is formed eccentrically by staggering the lateral guide slots in relation to the fixation thread.

BRIEF DESCRIPTION OF THE DRAWINGS

The invention will be discussed in greater detail by reference to the accompanying drawings, which show a particularly preferred embodiment of the invention, in which:

FIG. 1 is a perspective view of the device embodying the invention with one wedge only; no attached plaster cast has been drawn in;

DESCRIPTION OF THE PREFERRED EMBODIMENTS

Figure 1:
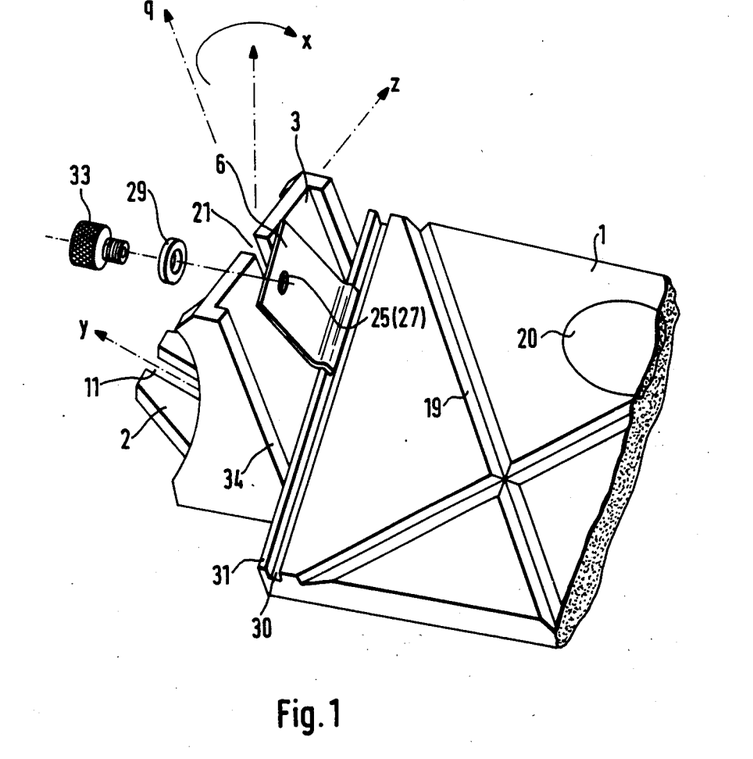

FIG. 1 is a perspective view of the device of the invention with only one wedge 3 for the sake of clarity. Wedges 3 can be moved longitudinally to "y" in the guide slot 11 of the base plate 2 and transversely to "z" through a slotted hole not shown herein and it can be rotated axially about "x". Thus, wedge 3 can be adjusted to any desired spatial position of the cast plate 1, which preferably has a trapezoidal shape.

In the slotted hole 21 of the wedge 3, which is open at the top, a fixation element 6, e.g., a fixation plate 6, is mounted with allowance for slidable movement between the ribs 34 by means of a threaded bore 25 and screw 33 or threaded pin 27 by means of a knurled nut 4.

The adjustability of the cast plate 1 in any necessary plane is made possible by the interplay between the individual elements described above, so that the specific jaw position of the patient is simulated exactly.

Figure 2:
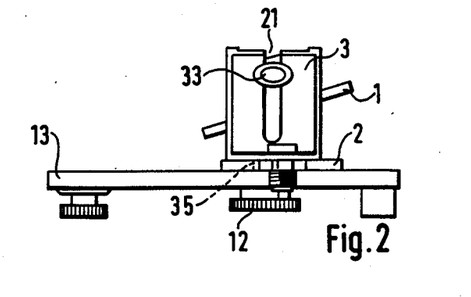
FIG. 2 is a side view of the device according to the invention mounted on a conventional articulator cast.
Figure 3:
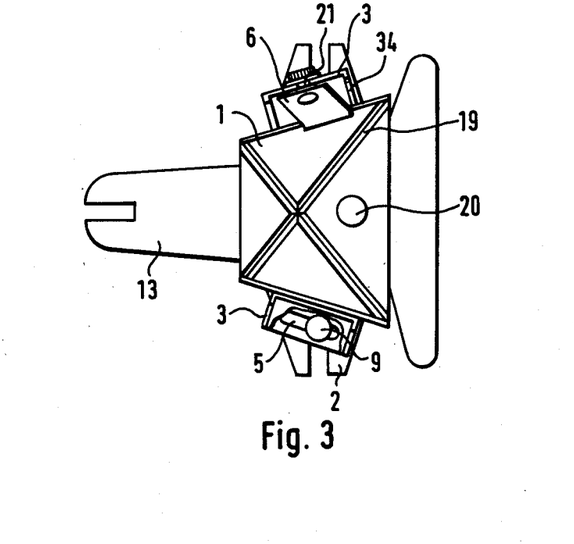
FIG. 3 is a top plan view of FIG. 1, without the front fixation element (6) in order to better show the screw (9) in the slotted hole (5) of the wedge (3)

FIGS. 2 and 3 are, respectively, an elevation and a top plan view of the subject of the invention mounted on a conventional device.

The baseplate 2 is mounted on a conventional type of articulator 13 by means of a knurled screw 12 and its fixation thread 35.

The cast plate 1 is clamped into position between the two wedges 3, thereby offering a seating surface that is locked against movement of the casts that are to be worked on.

The screw 9 that serves to lock the wedge frame is inserted into the slotted hole 5 shown in FIG. 3. Its formation will be described further in FIG. 4.

A particular feature of the invention is characterized by the fact that the wedges can be moved transversely to "y", longitudinally to "z" and can be rotated axially about "x" (cf. FIG. 1). Because the fixation plates 6 can also be moved to "q" in the direction of wedge action, the unrestricted adjustment of the cast plate 1 is ensured.

Figure 4:
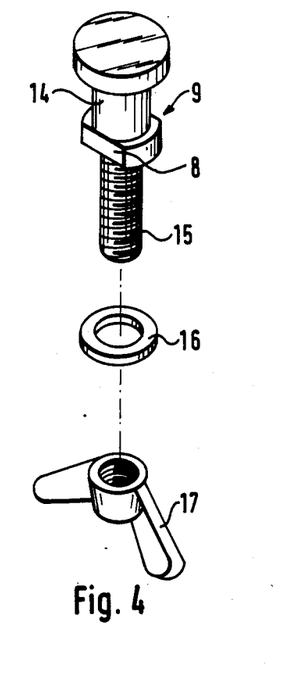
FIG. 4 shows the connecting screw of the wedge frame on the base platform.

FIG. 4 shows the connecting screw 9 between wedge frame 3 and base plate 2. It is provided with a plain cut 8 made in the guide slot 10, 11 of the base plate 2. A torque applied on the wedge frame by activation of the screw is thus ruled out.

The stem 14 serves for the guidance in the slotted hole 5 of the wedge 3. A wing nut 17 provided with a washer 16 or a knurled nut 44, in some cases with a key face, is screwed onto the thread 15 and the wedge frame is fixed as a result.

Figure 5:
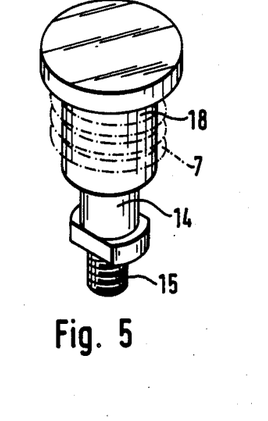
FIG. 5 is a modification of this screw guide, a helical spring being shown here for the spring bias.

FIG. 5 shows a modification of the screw described earlier, in which the stem 18 is pulled higher and is surrounded by a spring 7 to ensure spring bias of the wedge frame on the base plate.

Figure 6:
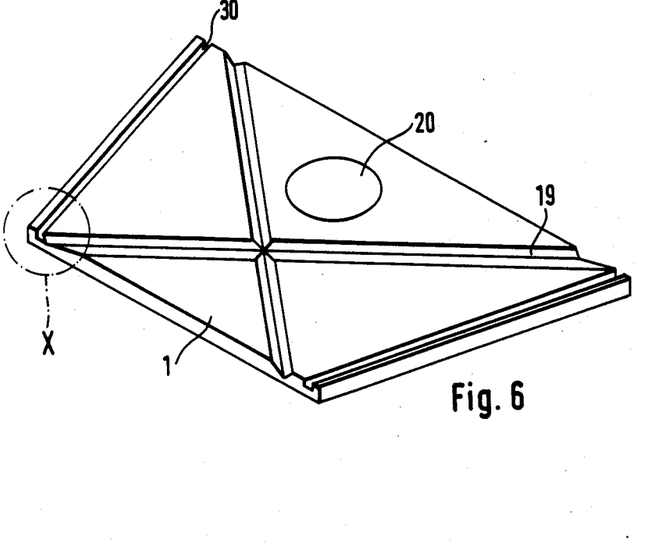
FIGS. 6, 6a and 6b are perspective views of the cast plate 6a and 6b showing variants of a detail "x" shown in FIG. 6.

FIG. 6 shows the perspective view of the cast plate 1 with milling 30. Further details for the direct fixing of the plaster casts, e.g. retention elements for plaster or fixation aids for cast systems are shown symbolically.

Figure 6A:
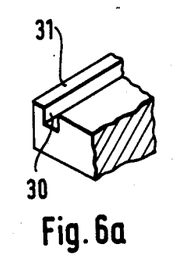
Figure 6B:
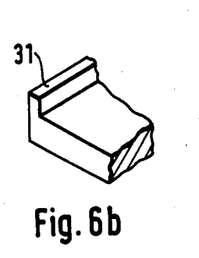

FIGS. 6a and 6b show a detail "x" from FIG. 6. Thus, the construction with a rib 31 and milling 30 (FIG. 6a) or only with rib 31 (FIG. 6b) is possible.

Figure 7:
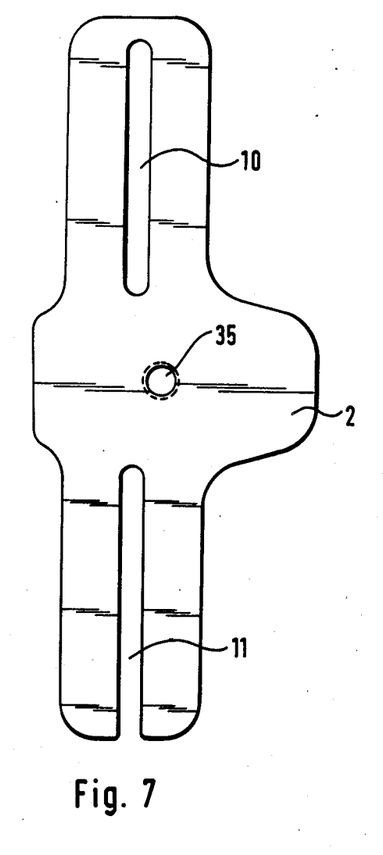
FIG. 7 shows the base plate.

FIG. 7 shows a particularly preferred embodiment of the base plate 2, in which the lateral guide slots can be open (11) or closed (10). A special feature is the fact that the base plate 2 is designed to be eccentric, inasmuch the guide slots are staggered in relation to the fixation thread 35. This produces a spatial advantage inasmuch as the base plate can be rotationally mounted by 180 degrees.

FIGS. 8–15 show a particularly preferred embodiment of the wedge 3 and of the fixation element 6 associated therewith. In this embodiment, the wedge 3 has an inclination face 22 arranged perpendicularly to the side walls 32 with a rib 34 on either side and a slotted hole 21 which is open at the top, in which the fixation element 6 is guided.

Figure 13:
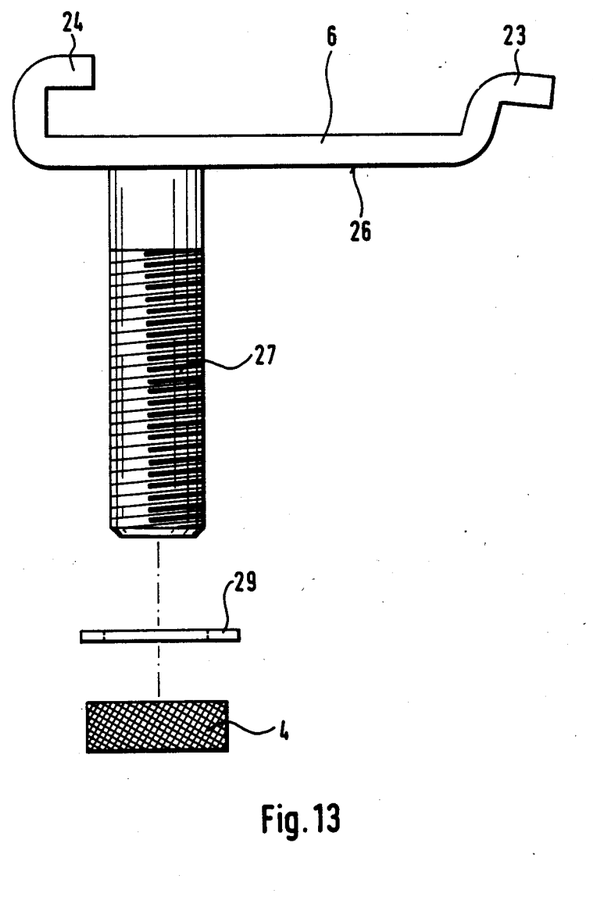
FIGS. 13–15 show modifications of the fixation element.
Figure 14:
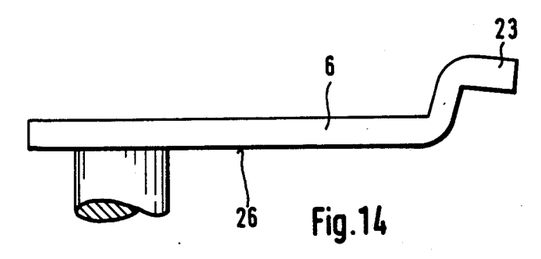
Figure 15:
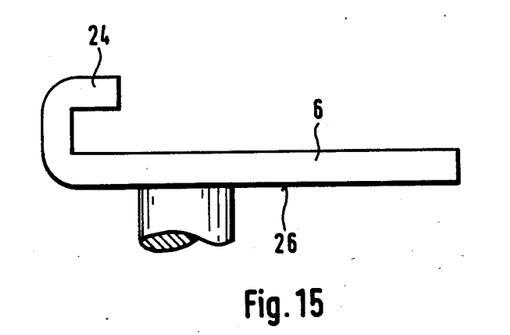

The locking of the fixation element 6 can be carried out on the one hand by a knurled screw 33 with a washer or a spring retainer (FIG. 8), whereby, on the one hand, a threaded bore 25 has been cut in the fixation element 6 and, on the other hand, it is possible to arrange a threaded pin 27 on the fixation element 6, which results in locking by a screwed-on knurled nut 4 with washer or spring retainer 29 (FIG. 13).

Figures 8, 9, 10, 11, 12:
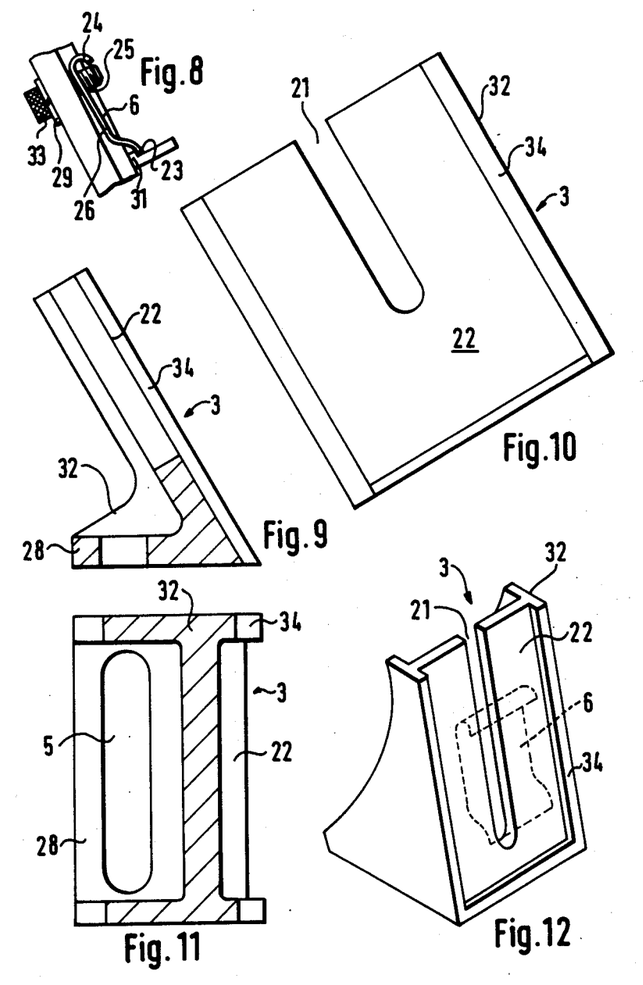
FIGS. 8–12 show a preferred embodiment of the wedge.

The retainer clamps 23, 24 engage the milling 30 or the rib 31 of the cast-support plate 1 and fix the the latter by tightening the screw 33 or the knurled nut 4, here optionally with a key face.

The fixation element 6 has different designs. According to a preferred embodiment, a fixation element 6 is formed with an upper retainer clamp 24 (FIG. 15) or with a lower retainer clamp 23 (FIG. 14), and another embodiment with an upper retainer clamp 24 and a lower retainer clamp 23 (FIG. 13).

The invention was described above with reference to one embodiment. It is obvious that this does not limit the scope of protection of the invention. Thus, instead of the wedge shape described above, one may also contemplate an embodiment in which the wedge frame is closed or open, and which, for the purpose of fixing cast plates, are arranged on the side and carry fixation elements in the form of fixation plates, which, provided with retainer clamps, secure the cast plate. Fixation aids are also possible, which operate according to the draw and set screw principle, or fixation aids in the form of screw tips, bores with incisions and retainer elements that can be moved and fixed therein.

Another preferred embodiment of the invention is shown in the accompanying FIGS. 16-19. This preferred embodiment for mounting jaw casts in an articulator is characterized by the fact that the device consists of an articulator mounting plate 100 (FIG. 16) and a cast plate 300 (FIG. 17), which can be allocated to each other by at least two wedges 1000 (FIG. 18), whereby the wedges 1000 can move in slotted guides 500 of the articulator plate 100 and can be pushed forward until they strike laterally against the cast plate 300, and draw and set screws 160, 280, 330 provided for the fixing.

Figures 16, 16A, 17:
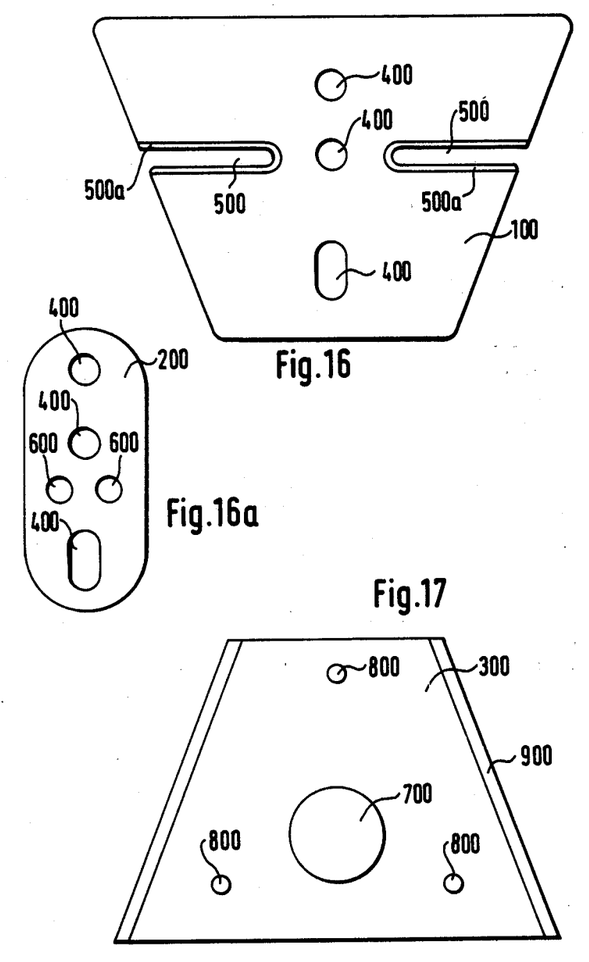
FIG. 16 is a plan view of an articulator mounting plate 100 in accordance with another embodiment of the present invention.
FIG. 16A is a plan view of a spacer plate 200 in accordance with another embodiment of the present invention.
FIG. 17 is a plan view of a cast plate 300 in accordance with another embodiment of the present invention.
Figure 18:
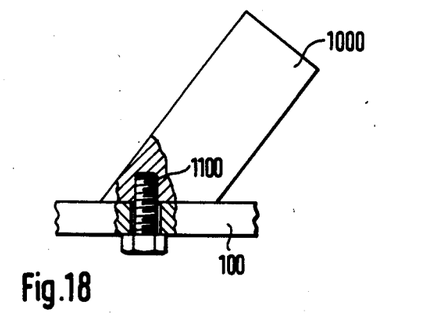
FIG. 18 is a side view, partially in crosssection, illustrating the connection between a wedge 1000 and the articulator mounting plate 100 of FIG. 16.
Figure 19:
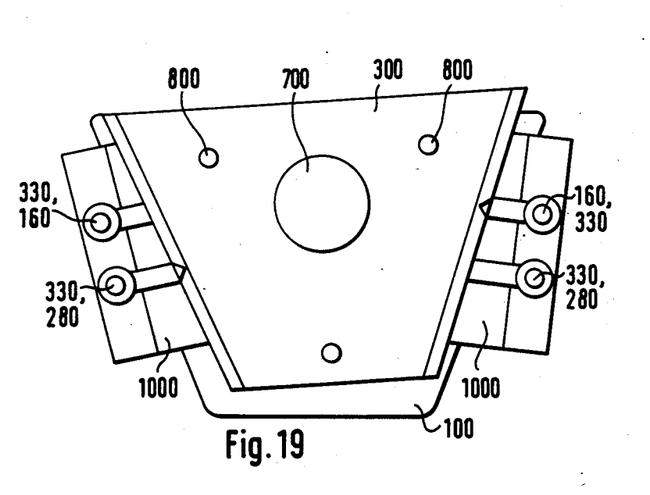
FIG. 19 is a plan view illustrating the overall connection of the embodiment in accordance with the present invention including the articulator mounting plate 100 of FIG. 16, the cast plate 300 of FIG. 17 and wedges 1000 of FIG. 18.

According to another embodiment, the device incorporating the invention is characterized by the allocation of the spacer plate 200 (FIG. 16a).

According to another preferred embodiment, the device of the invention is characterized by the fact that fixation aids 800 for cast systems are mounted on the cast plate 300.

According to another preferred embodiment, the device in accordance with the invention is characterized by the fact that the fixation aids 800 consist of bores, incisions, slots or screw tips.

According to another preferred embodiment, the device of the invention is characterized by the fact that a magnet 700 for mounting casts is arranged on the cast plate 300.

According to another preferred embodiment, the device of the invention is characterized by the fact that the wedge 113 is shaped like a rhomboid with a central recess 115, whereby the base has a slotted hole 116 and each of the obliquely positioned side walls 117 has a threaded bore 118 (FIGS. 20-23).

Figure 20:
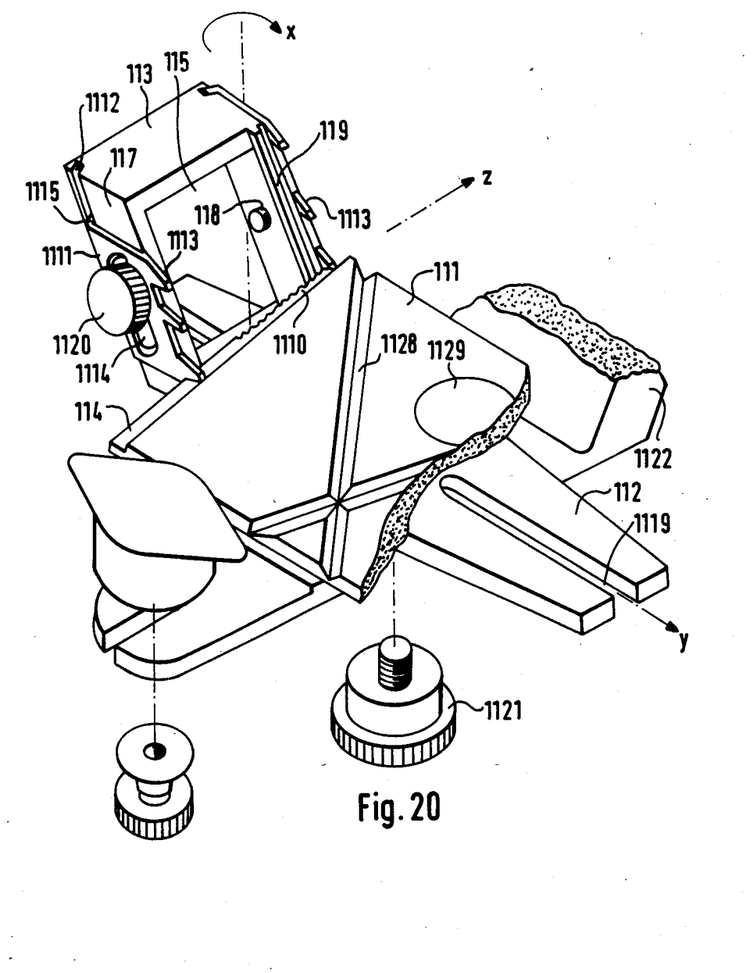
FIG. 20 is a partial perspective view of another embodiment of the present invention having a wedge 113 shaped like a rhomboid.
Figure 21:
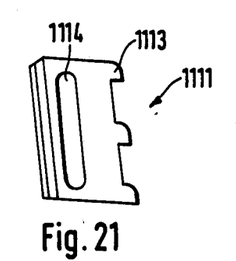
FIG. 21 is a side view of a sliding fixation element 1111 of FIG. 20.
Figure 22:
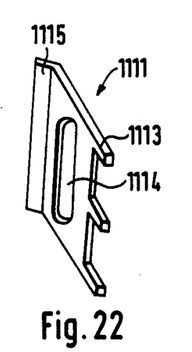
FIG. 22 is a perspective view of another embodiment of the sliding fixation element 1111.
Figure 23:
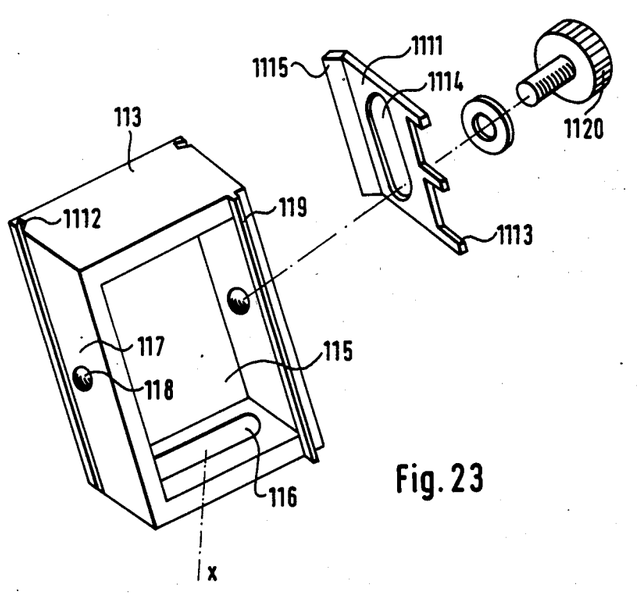
FIg. 23 is an exploded perspective view for illustrating the connection between the sliding fixation element 1111 and the wedge 113 of FIG. 20.
Figure 24:
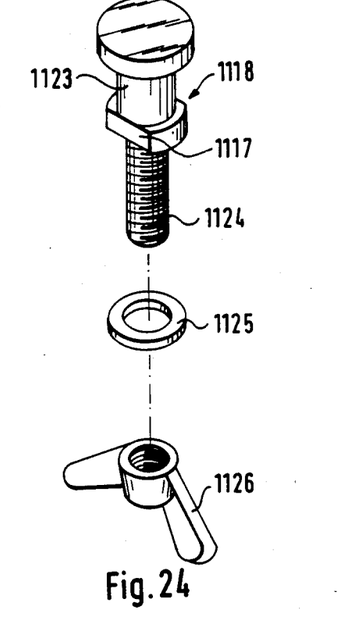
FIG. 24 is an exploded perspective view of a screw and wing nut for mounting on the base plate 112 of FIG. 20.
Figure 25:
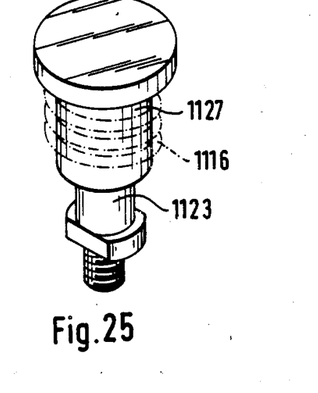
FIG. 25 is a perspective view for illustrating the spring bias of the screw which is mounted to the base plate.

According to another preferred embodiment, the device of the invention is characterized by the fact that the sliding fixation elements 1111 are shaped like rhomboids and preferably have three projecting lugs 1113 that point to the cast plate 111, as well as a slotted hole 1114 that serves for their mobility, whereby the boundary opposite the lugs has a guide bend or guide milling 1115, which is obliquely congruent with the milling 1112 of the wedge 113 (FIG. 20).

According to another preferred embodiment, the device of the invention is characterized by the fact that the slide-shaped fixation elements 1111, by means of a preferably knurled screw 1120 guided through their slot 1114 and engaging the threaded bore 118 of the wedge 113, can be fixed to the cast plate 111 after a lug 1113 has struck against the cast plate 111.

According to another preferred embodiment, the device of the invention is characterized by the fact that the cast plate 111 has a trapezoidal shape and has a toothing 1110 on either side.

According to another preferred embodiment, the device of the invention is characterized by the fact that the toothing consists of at least one partially toothed rib 114.

According to another preferred embodiment, the device of the invention is characterized by the fact that the wedge 113 has a rib 119 that runs in effective surface of the wedge, which engages the toothing 1110 of the cast plate 111.

According to another preferred embodiment, the device of the invention is characterized by the fact that the wedge 113 has on either side an oblique milling 1112, in which the fixation elements, preferably fixation plates 1111, are mounted to be moved in the manner of a slide in wedge action, and which prevent a torque from being applied on the fixation element upon activation of the knurled screw.

According to another preferred embodiment, the device of the invention is characterized by the fact that the slide-shaped fixation elements 1111, by means of a preferably knurled screw 1120 which is guided through their slotted hole 1114 and engages the threaded bore 118 of the wedge 113, can be fixed after a lug 1113 has struck against a cast plate 111.

According to another preferred embodiment, the device of the invention is characterized by the fact that the wedges are secured with allowance for adjustment to the base plate 112 by a wing nut 1126, preferably through spring bias 1116 of a screw 1118 running in the base plate 112 and guided spin-safe by a screw milling 1117.

According to another preferred embodiment, the device of the invention is characterized by the fact that the base plate 112 is provided on either side with a guide slot 1119 which is open to the side.

These other preferred embodiments are shown in the accompanying FIGS. 19-25.

WHAT IS CLAIMED IS:

1. A device for mounting jaw casts in an articulator, comprising:
   a cast plate for supporting a jaw cast;
   an articulator base plate;
   inclined members adjustably connected to said articulator base plate, each of said inclined members being longitudinally and transversely movable and axially rotatable; and
   fixation elements, each of which is slidably connected to said cast plate and adjustably connected to a corresponding one of said inclined members, said fixation elements slidably movable in the inclination of said inclined members and lockable in a predetermined position along said inclined members, said cast plate being pressed against said inclined members and fixed in position.

2. A device for mounting jaw casts as recited in claim 1, wherein said cast plate has a positive or negative relief which permits the direct plastering of the jaw cast, and is further suited to receive cast systems, and wherein said cast plate has a magnet to facilitate removal and safe return of the jaw cast to said cast plate.

3. A device for mounting jaw casts as recited in claim 1 or 2, wherein said base plate is provided with a guide slot on each side.

4. A device for mounting jaw casts as recited in claim 3, wherein each of said inclined members has:
an inclination face provided with a slotted hole which is open at the top;
side ribs, extending from said inclination face, on which said fixation element can be slidably moved; and
a bottom area extending from said inclination face and having a slotted hole to facilitate mounting to said articulating base plate.

5. A device for mounting jaw casts as recited in claim 4, further comprising:
a screw running in the guide slot of said articulator base plate and having a screw milling for guiding spin-safe through and locking said screw so that each of said inclined members can be located with allowance for adjustment;
a bias spring for biasing said screw; and
a wing nut or a knurled nut for threading on said screw which extends through the slotted hole of the bottom area so as to fix each of said inclined members on said articulator base plate.

6. A device for mounting jaw casts as recited in claim 1, wherein each of said fixation elements is formed as a sliding plate with a retainer clamp which is bent away in the lower region.

7. A device for mounting jaw casts as recited in claim 6 wherein said retainer clamp is bent away in the upper region.

8. A device for mounting jaw casts as recited in claim 1, wherein each of said fixation elements comprising a sliding plate with retainer claws.

9. A device for mounting jaw casts as recited in claim 6, 7 or 8, wherein each of said fixation elements has a threaded bore.

10. A device for mounting jaw casts as recited in claim 6, 7 or 8, wherein each of said fixation elements has a bearing face and a threaded pin mounted on said bearing face.

11. A device for mounting jaw casts as recited in claim 6 or 7, wherein said cast plate has a trapezoidal design and has on either side a milling which is arranged to locate said retainer clamp.

12. A device for mounting jaw casts as recited in claim 11, wherein said cast plate has a rib for fixing said cast plate by means of said retainer clamp.

13. A device for mounting jaw casts as recited in claim 3, wherein said articulator base plate has a fixation thread and wherein said articulator base plate is formed eccentrically by staggering said guide slot in relation to said fixation thread.

14. A device for mounting jaw casts in an articulator, comprising:
an articulator plate having slotted guides;
a cast plate for supporting a jaw cast;
inclined members adjustably connected to said articulator plate for movement in the slotted guides of said articulator plate, said inclined members being movable until they strike laterally against said cast plate; and
fasteners for fixing the position of said inclined members against said cast plate.

15. A device for mounting jaw casts in an articulator as recited in claim 14, further comprising a spacer plate positioned between said articulator plate and said inclined members.

16. A device for mounting jaw casts in an articulator as recited in claim 14, further comprising fixation aids arranged on said cast plate.

17. A device for mounting jaw cast in an articulator as recited in claim 16, wherein said fixation aids comprise bores, incisions, slots or screw tips.

18. A device for mounting jaw casts in an articulator as recited in claim 14, further comprising a magnet positioned on said cast plate for mounting a jaw cast.

19. A device for mounting jaw casts in an articulator as recited in claim 14, wherein each of said inclined members comprises a frame designed in the form of a rhomboid with a central recess, said frame having a base with a slotted hole, and obliquely positioned side walls extending from said base, each of said slide walls having a threaded bore.

20. A device for mounting jaw casts in an articulator as recited in claim 19, wherein each of said inclined members has a milling, further comprising fixation elements, shaped like rhomboids and movable like a sled, wherein each of said fixation elements has three lugs that protrude in the direction of said cast plate, as well as a slotted hole used for mobility, wherein said cast plate has a guide bend or guide milling at its boundary opposite the lugs, and wherein said guide bend or guide milling is obliquely congruent with the milling of each of said inclined members.

21. A device for mounting jaw casts in an articulator as recited in claim 20, further comprising a knurled screw extending through the slotted holes of the sled-shaped fixation elements to engage the threaded bore of one of said inclined members after one of said lugs has contacted said cast plate.

22. A device for mounting jaw casts in an articulator as recited in claim 14, wherein said cast plate has a trapezoidal shape and a toothed portion on one side of said cast plate.

23. A device for mounting jaw casts in an articulator as recited in claim 22, wherein the toothed portion comprises at least one partially toothed rib.

24. A device for mounting jaw casts in an articulator as recited in claim 23, wherein each of said inclined members has a rib that runs in the effective face of the inclined member, which engages the toothed portion of said cast plate.

25. A device for mounting jaw casts as recited in claim 21, wherein said fixation elements comprise fixation plates which are mounted with allowance for sled-like movement in wedge action, and which prevent a torque from being applied on said fixation elements.

26. A device for mounting jaw casts as recited in claim 25, wherein each of said inclined members has a threaded bore and wherein each of said sled-like fixation elements has a slotted hole, further comprising knurled screws guided through the slotted hole and engaging the threaded bore of each of said inclined members respectively after one of said lugs has struck against said cast plate.

27. A device for mounting jaw casts in an articulator as recited in claim 14, further comprising:
    a wing nut;
    a base plate; and
    a screw running in said base plate, said screw being spring biased and being guided spin-safe through a screw milling, wherein each of said inclined members is mounted with allowance for adjustment and can be fixed on said base plate by said wing nut.

28. A device for mounting jaw casts in an articulator as recited in claim 27, wherein said base plate is provided on either side with a guide slot which is open to the side.

* * * * *